(12) United States Patent
Nistal (10) Patent No.: US 7,485,127 B2
(45) Date of Patent: Feb. 3, 2009

(54) TUBULAR TORQUE TRANSMITTING SYSTEM FOR MEDICAL DEVICE

(75) Inventor: Brent Nistal, Seattle, WA (US)

(73) Assignee: Pathway Medical Technologies, Inc., Kirkland, WA (US)

( * ) Notice: Subject to any disclaimer, the term of this patent is extended or adjusted under 35 U.S.C. 154(b) by 1069 days.

(21) Appl. No.: 10/798,622

(22) Filed: Mar. 10, 2004

(65) Prior Publication Data

US 2004/0235611 A1  Nov. 25, 2004

Related U.S. Application Data

(60) Provisional application No. 60/453,846, filed on Mar. 10, 2003.

(51) Int. Cl.
*A61B 17/14* (2006.01)
(52) U.S. Cl. .................................................. 606/180
(58) Field of Classification Search ................. 606/159, 606/167, 168, 170, 174, 180, 1; 604/164.01, 604/264, 523; 279/61, 62, 140
See application file for complete search history.

(56) References Cited

U.S. PATENT DOCUMENTS

| 4,445,509 | A | 5/1984 | Auth |
| 5,314,407 | A | 5/1994 | Auth et al. |
| 6,080,170 | A | 6/2000 | Nash et al. |
| 6,565,588 | B1 | 5/2003 | Clement et al. |
| 2002/0007190 | A1 | 1/2002 | Wulfman et al. |
| 2004/0006358 | A1 | 1/2004 | Wulfman et al. |

FOREIGN PATENT DOCUMENTS

EP  0 409 372 A1  1/1991

*Primary Examiner*—Kevin T. Truong
(74) *Attorney, Agent, or Firm*—Speckman Law Group PLLC (57) ABSTRACT

A torque transmitting system supports rotational and lateral movement of a drive shaft. The system includes translating inner and outer tubes which have aligned canals for placement of a ball bearing and a pinion shaft to couple the tubes to a drive system. Rotational torque is transferred from the pinion shaft, to the outer tube and, through the ball positioned in the aligned canals, to the inner tube and then to the drive shaft. Furthermore, the ball engaged in the canals defines a range of motion in which the inner tube is slidable with respect to the outer tube, along the tubes' longitudinal axis, to permit advancement of an attached drive shaft.

12 Claims, 10 Drawing Sheets

TUBULAR TORQUE TRANSMITTING SYSTEM FOR MEDICAL DEVICE

CROSS-REFERENCE TO RELATED APPLICATIONS

This application claims priority from U.S. Provisional Patent Application No. 60/453,846, filed Mar. 10, 2003. The disclosure of this application is incorporated herein by reference in its entirety.

FIELD OF THE INVENTION

The present invention relates to a bearing system for transferring torque from a motor to a drive shaft. The present invention is particularly useful in the medical field for advancing a catheter and/or drive shaft into a body while maintaining connection between the drive shaft and a drive system. It is to be understood that the terms "medical field" and "medical device", as used herein, include traditional medicine as well as alternative medicines including chiropractic, acupuncture, etc., as well as the veterinary field.

BACKGROUND

In many intracorporeal devices in the medical field, an operating head that is attached to an end of a drive shaft must be both rotated and advanced into a body in a controlled manner to perform a medical procedure. For many medical devices, control of the device's movement in the body is manifestly critical to the safety and reliability of the devices. For example, uncontrolled movements may cause damage to healthy tissue in the body. It is desirable for the drive shaft to smoothly transmit rotational torque from a drive system to the operating head. At times, the drive shaft may need to operate at high speeds, such as about 500 to 200,000 rpm's. The connection between the drive system and drive shaft must be able to accommodate these high speeds, and yet, maintain steady torque transmission.

Furthermore, some medical procedures require advancement of a lightweight rotating system to or through a treatment site, where advance motion of the rotating drive is independent of a heavy motor drive system, as well as independent in motion relative to a guidewire over which a device travels. Furthermore, some treatments require a delicate interaction and thus mandate low inertial masses of the rotating drive system, requiring a drive transmission to be small and efficient. Moreover, some medical procedures require the operator to use tactile sensitivity in holding the device to assess the operation of the device. Therefore, interferences due to rickety rotational torque may disturb the operator's tactile sense or cause other interruptions of the operation.

Intracorporeal medical devices that include drive shafts are employed for therapeutic and/or diagnostic procedures. Particular methods of using atherectomy and thrombectomy devices involve placement of a guiding catheter into the body and insertion of a guidewire, over which the operating head attached to the drive shaft is guided to a target site where an occlusion is located within a blood vessel. However, devices that do not employ guidewires are also possible. The drive shaft extends within the lumen of an operating catheter to effectively isolate the rotating elements of the device from direct contact with any healthy body matter, e.g. tissue. The catheter is fixed to the operating head at its distal end in a manner that maintains the catheter in a static position relative to the rotating drive shaft and maintains the seal of the catheter lumen. The operating head is advanced and rotated to cut or ablate the obstruction and to restore or improve blood flow in the vessel.

A general challenge of operating an intracorporeal device is that it is often difficult to guide the operating head attached to the drive shaft and/or catheter through the body to reach the area of interest, i.e. target site. The intracorporeal device must usually be routed along a tortuous path, through various internal structures within the body before arriving at the target site. For example, an obstructed blood vessel may be located in peripheral vessels, coronary vessels, cranial vessels, or other areas. The path may be of varying lengths depending on where the target site is relative to the site in the body for insertion of the intracorporeal device, i.e. insertion site. For example, the device is often inserted into a leg of a patient and then directed to the heart, head, other leg, kidney, etc. It is beneficial, then, for the intracorporeal device to allow for varying lengths of catheter and drive shaft to be inserted in the body.

During the operation, it is often necessary to move the operating head back and forth to properly operate on the target site. The intracorporeal device should provide for a means to control a smooth back and forth motion in a manner that produces little friction. Moreover, at times, unwanted matter may need to be removed from the target site by the device and the matter may be various sizes and shapes and positioned at varied locations within the body cavity. The device should allow for extended lengths to be inserted in the body during the operation, such as for cutting of the large masses of matter.

In order to advance the catheter into the body, the guidewire must be fed in a distal direction in order to maintain the position of the guidewire relative to the target site. To address the need to provide extra lengths of catheter and drive shaft, such as during the cutting of long masses, some current devices provide for a limited extra length of catheter, when required, by a sliding member housed within a handheld device. The device must accommodate such sliding of the catheter without disengaging the drive shaft from the drive system. The drive system may need to be slid with the catheter movement. The extension amount is limited by the size of the handheld device and the handheld device may need to be large to accommodate sliding of the catheter. However, a larger handheld device is not usually desirable, especially for a target site that is located far away from the insertion site, because the hand held is placed close to the body and, as a result, there may be a shortage of guidewire length to be pulled as the catheter is advanced.

It is therefore desirable to provide a small, lightweight torque transmission system that allows a driven system to be moved axially relative to a motor drive system where the movement is free of significant friction such that motion is unimpeded and free, even when significant torque loading of the drive system occurs. The connection between the drive shaft and drive system should provide for smooth translation of drive shaft and advancement of the catheter without disengaging from the drive shaft. The system should permit movement with low production of friction. The present invention fulfills these needs and provides further related advantages.

SUMMARY

In many interventional catheter systems of intracorporeal medical devices, rotational torque must be delivered to a drive shaft from a drive system. For devices with advanceable, rotatable operating heads, the transfer of torque must be accomplished so that the drive shaft is simultaneously advanceable and rotatable. Mounting of the drive shaft off-axis with respect to the output shaft of the drive system using suitable gearing systems permits translation and advancement of the drive shaft independently from the drive system, which allows the drive system to remain stationary during operation of the interventional catheter.

In one embodiment of a torque transfer system of the present invention, a torque transfer sliding tube system is provided for transferring torque to the drive shaft. The torque transfer system both provides torque to the drive shaft and permits smooth axial translation of the drive shaft, even at high rotational speeds. The sliding tube torque transfer system also allows the catheter system to advance over a guidewire without the drive shaft disengaging from the drive system and while a guidewire locking device maintains the guidewire position. Experimental work has also demonstrated that the sliding tube torque transfer system of the present invention may provide an operator greater and more realistic tactile feel for safe and effective removal of undesired material during operation of the operating head as the lesion when a sliding tube torque transfer system is used in the interventional catheter assembly.

The torque transmitting system comprises a rigid inner tube or cylinder and a rigid outer tube or cylinder that is axially slidable over at least a portion of the inner tube. Each of the tubes is provided with at least two matching canals generally arranged in a radially symmetrical arrangement, with a ball bearing being slidably retained between each set of canals. The inner and outer tubes are sized so that when a ball bearing is placed between each of the matching canals, the tubes are both axially slidable and rotatable with respect to one another. The canal in the form of a groove usually extends for most of the length of inner tube, so that the inner and outer tubes are slidable with respect to one another along most of the length of inner tube. The canal in the form of a slot of the outer tube usually extends through the body of the tube and does not include a bottom surface.

A proximal end of the outer tube may be operably coupled to a pinion shaft of the drive system. The pinion shaft transfers torque to the outer tube and retains the ball bearings. The pinion shaft includes at least one gear to operatively couple to a drive system gear. Rotational torque is transferred from the pinion shaft, to the outer tube and, through the ball bearings being positioned in the aligned canals, to the inner tube and then to a drive shaft. The catheter system may be mounted to the inner tube, such as through a main shaft, which allows smooth translation of the catheter even during high rotational operations.

In one embodiment, a sealing member couples to the catheter and is slidable in a movement that coincides with the sliding of the inner tube of the transmission system. The device may further comprise a hand held device to house the sealing member, drive system and/or transmission system. Furthermore, some devices include a console unit to control the drive system.

BRIEF DESCRIPTION OF THE DRAWINGS

The present invention is illustrated by way of example in the figures of the accompanying drawings and the figures are not intended for limitation, which figures are not intended to limit the present invention, and in which:

FIGS. 4A-4B are schematic diagrams illustrating inner and outer tubes and ball of a torque transmission system, wherein FIG. 4A shows the tubes in a retracted position and FIG. 4B shows the tubes in an extended position;

FIGS. 5A-5B are schematic diagrams illustrating a torque transmission system coupled to a drive system, wherein FIG. 5A shows the system in a retracted position and FIG. 5B shows the system in an extended position;

FIGS. 7A-B are a schematic diagrams of side plan views from proximal to distal end of some separated components of the torque transmitting system, wherein FIG. 7A shows the ball bearing within the inner tube grooves and pinion shaft, and FIG. 7B shows the ball bearings within the outer tube slots;

DETAILED DESCRIPTION

The torque transmitting system of the present invention includes translating inner and outer tubes which have canals for placement of a ball bearing and a pinion shaft to couple the tubes to a drive system. The canals of the tubes are aligned and sized to permit the ball to move with little friction. Rotational torque is transferred from the pinion shaft, to the outer tube and, by way of the ball positioned in the aligned canals, to the inner tube and then to a drive shaft. Furthermore, the ball engaged in the canals defines a range of motion in which the inner tube is slidable with respect to the outer tube, along the tubes' longitudinal axis, to permit advancement of an attached drive shaft. In this manner, the transmission system supports rotational and lateral motion of a drive shaft.

The torque transmission system is useful in a variety of intracorporeal medical devices employing a drive system to rotate a drive shaft that also requires lateral motion. The intracorporeal medical device incorporating the torque transmitting system of the present invention may be implemented for treatment or diagnosis in a variety of surgical operations and procedures, such as translumenal microsurgery. For example, the system may be used in the treatment of blood vessel conditions, such as removal of accumulations of materials in coronary blood vessels and in blood vessels remote from the heart. Other applications include, and are not limited to, the treatment or diagnosis of benign prostate hyperplasia; gynecological conditions involving accumulation of material in fallopian tubes and elsewhere, such as fibrotic disease; urological conditions, such as kidney stones; the treatment of gallbladder conditions, such as gall stones; and spinal cord and dural tube conditions, such as stenoses of the spinal canal. Medical fields of use include cardiology, radiology, urology, neurology, etc.

In general, the drive shaft of the intracorporeal device may need to be advanced into any body cavity that has a sufficiently hollow space to accept an operating head attached to the drive shaft. Some body cavities include a vascular cavity, gastrointestinal cavity, air exchange cavity, or the like. The body cavity may be a tubular-shaped structure, such as an artery, a vein, or another blood vessel, or another lumen structure, such as a ureter, a fallopian tube, a nasal passageway, and other tubular tissues in a body. For example, the system may be used for removing unwanted material in saphenous vein graft operations, from native coronary (and other) arteries, etc. The body cavity may also be an organ, such as a kidney, gall bladder, lung, or the like, or the body cavity may form part of another system, such as a lymph node, spinal canal, etc. The term "body", as used herein, includes that of a human being or another animal subject.

As used herein to describe various components of the intracorporeal device including the torque transmitting system affixed to the intracorporeal device, the term "proximal" refers to a direction or area away from the end of the device to be first inserted into a body, and "distal" refers to the direction or area toward such insertion portion.

Figure 1:
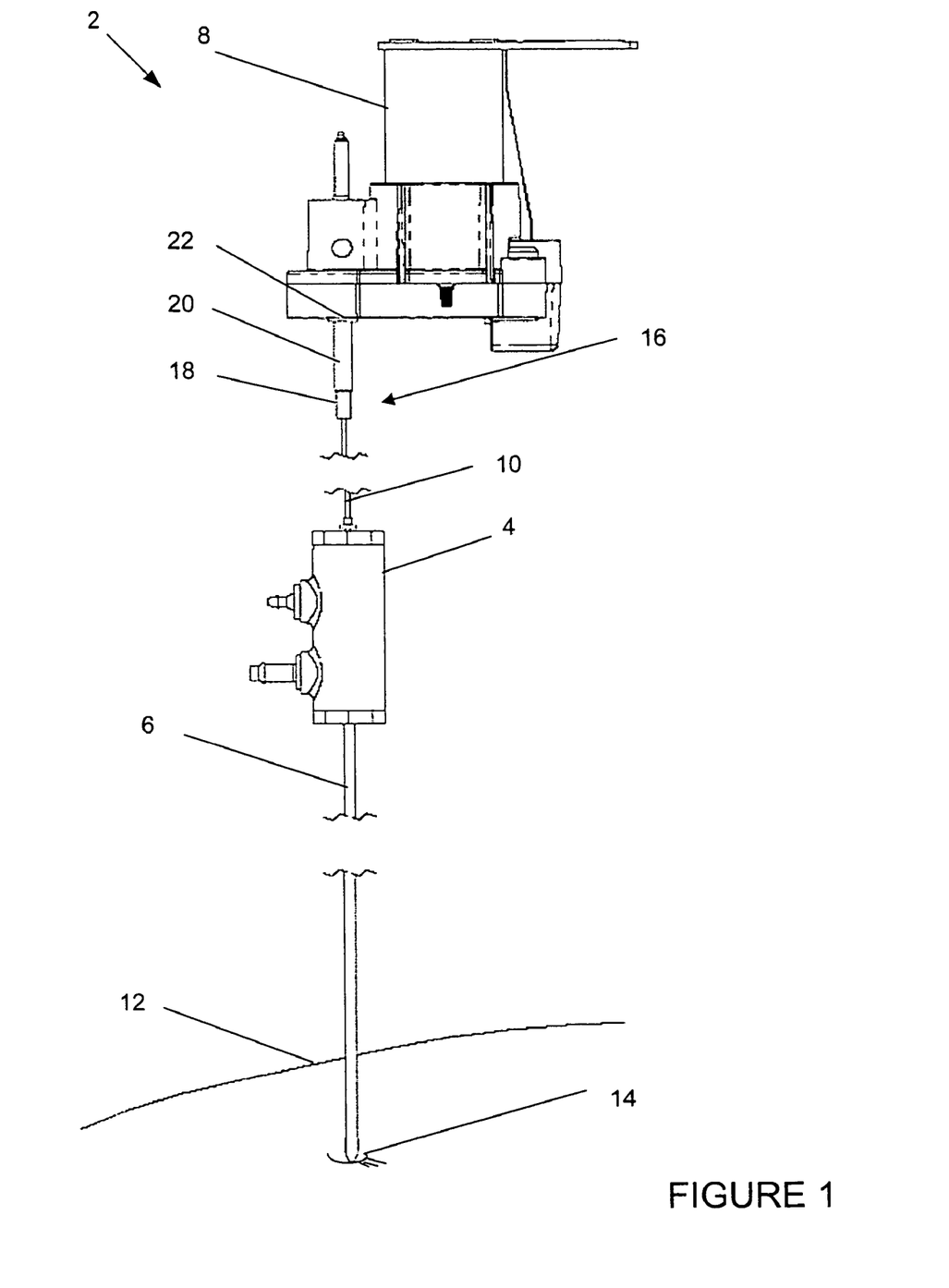
FIG. 1 is a schematic diagram of an top plan view of components that are external to a body of an intracorporeal medical device that implements a torque transmission system according to one embodiment of the present invention.

One particular intracorporeal device 2 that may incorporate a torque transmitting system 16 of the present invention is shown in FIG. 1 by example. The device has a drive shaft extending from the transmitting system, and within a catheter 6, to inside of a patient's body. The medical device includes components that are inserted and navigated within the patient's body while an operator uses the intracorporeal device, and these components are generally continuous with and/or in communication with components for placement external to the patient.

The extracorporeal components of the intracorporeal device 2 essentially comprise a torque transmission system 16 that conveys rotational torque from a drive system 8 to the drive shaft at the proximal end of the drive shaft. The torque transmission system includes an inner tube 18 that is slidable within an outer tube 20. A pinion shaft 22 is partially inserted within the housing of the drive system 8 and partially mounted to the outer tube 20. The term "mounted" and variations thereof is to be understood to include direct mounting of components and indirect mounting to any intermediary member that may be present between the components. One embodiment of the torque transmission system includes an optional main shaft 10 fixed to the proximal portion of the drive shaft that attaches to the inner tube. The drive shaft may be contained within a catheter 6 from a sealing assembly 4 and extending distally into the body 12. The catheter enclosing the drive shaft is inserted into the body at an insertion point 14.

The drive system 8 may be a motor e.g. an electric motor or a pneumatic-powered motor. Oftentimes, the drive shaft may be rotated at high speed of 500 rpm to 200,000 rpm, more typically about 10,000 to 100,000 rpm and more often about 40,000 rpm. However, the drive system is also intended to include various mechanical devices that rotate the drive shaft at any convenient speed. For example, for some thrombectomy procedures, low rotational speed, e.g. 10-20 rpm, may be desirable to break up particles aspirated into the device.

The drive shaft 10 may be any elongated tube that is rotatable. Oftentimes, the drive shaft comprising multiple coils or filars and is often a flexible, hollow, helical, torque-transmitting shaft. Hollow, multi-filar metallic drive shafts are known in the art and are suitable since the present sealing assembly permits sealing of non-solid shafts as well as solid shafts. A multi-filar stainless steel coil drive shaft having a bi- tri- or quad-filar construction is often employed. A coil drive shaft having an inner diameter of from about 0.015 to 0.025 inch and an outer diameter of from about 0.025 to 0.035 inch is typical for atherectomy applications.

Figure 2:
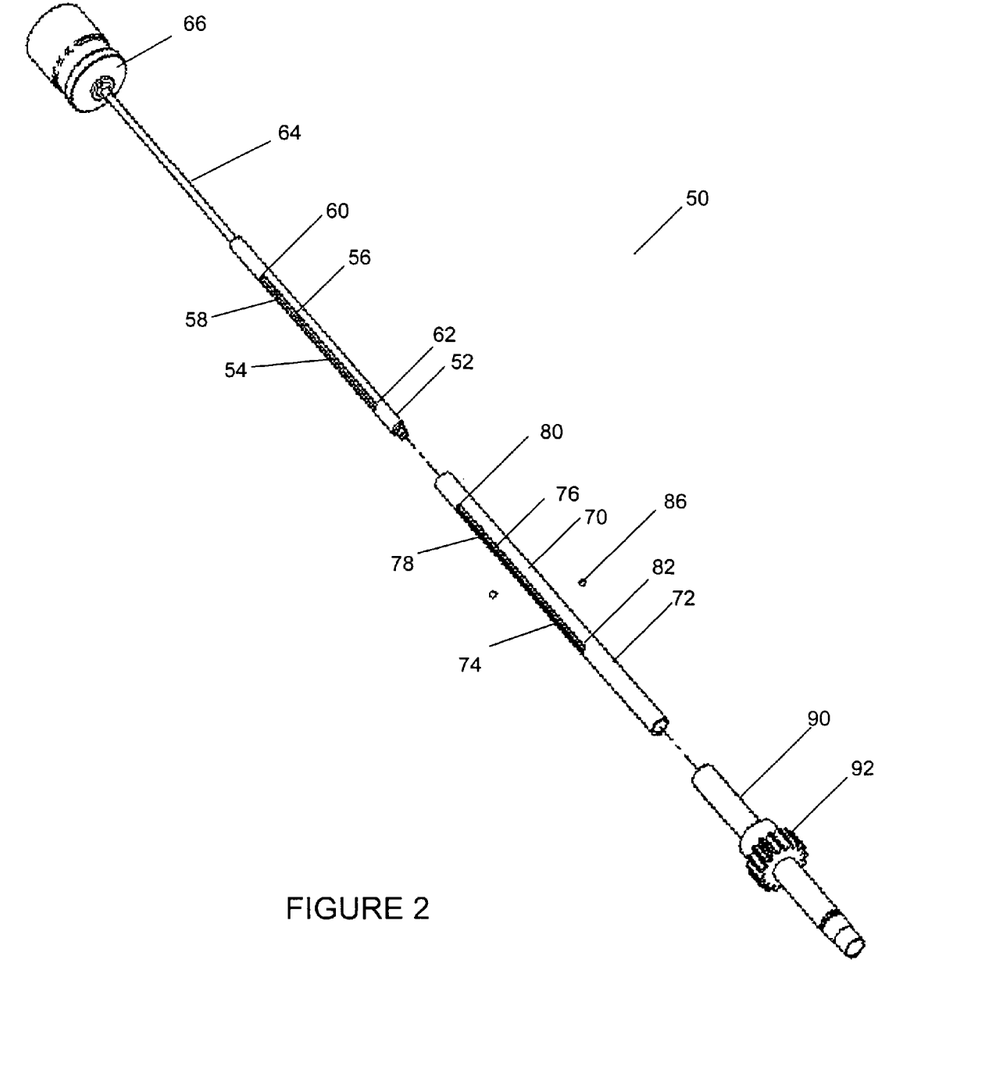
FIG. 2 is a schematic diagram of exploded components of the torque transmission system of FIG. 2.

As shown by the view of exploded components of a torque transmission system 50 in FIG. 2, the inner tube 52 has at least one groove 54 extending along a portion of the longitudinal length of the inner tube. Typically two grooves are provided on opposing sides around the diameter of the inner tube. The groove is defined by two opposing side walls 56, 58 along the length of the groove, two opposing end walls, 60, 62 and a bottom surface sunken within the body of the inner tube. The inner tube may comprise any convenient material that is capable of withstanding the desired amount of torque. Often, the inner tube is a metal, e.g. steel.

In some embodiments of transmission system, the inner tube directly mounts to the drive shaft. In other embodiments, an intermediary component is mounted between the inner tube and drive shaft. For example, a main shaft 64 may be coupled to the distal end of the inner tube 52 and encase the drive shaft. The main shaft may be secured to the drive shaft, e.g. via welding, such that the main shaft rotates the drive shaft. The main shaft 64 may also be affixed to one or more retainers 66 associated with an extension system of the intracorporeal device. The retainer is secured the drive shaft to prevent the drive shaft from disengaging from the drive system as the drive shaft is advanced.

The transmission system further includes the outer tube 72 having at least one slot 74 cut through the thickness of the tube and extending along a portion of the longitudinal length of the inner tube. A body 70 of the outer tube supports the slot. The slot is defined by two opposing side walls 76, 78 along the length of the groove, two opposing end walls, 80, 82. The slot usually extends through the body 70 and does not include a bottom surface. The outer tube further includes a lumen extending through the length of the outer tube. The diameter of the lumen is sufficiently larger than the outer diameter of the inner tube to permit the inner tube to extend within the lumen as well as the ball bearing to fit within both the slot of the outer tube and the groove of the inner tube.

The width of the slot is usually slightly larger than the diameter of the ball to create some play between the ball and the slot and reduce friction. However, the width of the slot is not so large as to excessively reduce the thickness of the body 70 and make the body too fragile to withstand the desired amount of torque. Furthermore, any number of slots may be provided without being too numerous as to make the body also too thin to withstand the torque. Typically, two opposing slots are included forming a hollow canal through the body.

The outer tube may comprise any convenient material that is capable of withstanding the desired amount of torque. Often, the outer tube is a metal capable of being welded to the pinion shaft, e.g. steel. The length of the outer tube is greater than the length of the slot. Usually, the length of the outer tube is greater than the length of the inner tube, such as about 0.10 inch longer than the length of the inner tube.

The ball bearings 86 may be any diameter ball that fits within the slot without falling through and permit a clearance between the groove sidewalls. For example, the ball diameter may be between about 0.020 and 0.040 inch and more typically between about 0.025 and 0.030 inch, e.g. about 028 inch. The ball may comprise any durable material that may withstand the rotational torque applied to the system. Any number of ball bearings may be employed and typically one ball engages one slot/groove combination. Often two balls are used, each ball positioned within each slot/groove.

Figure 3:
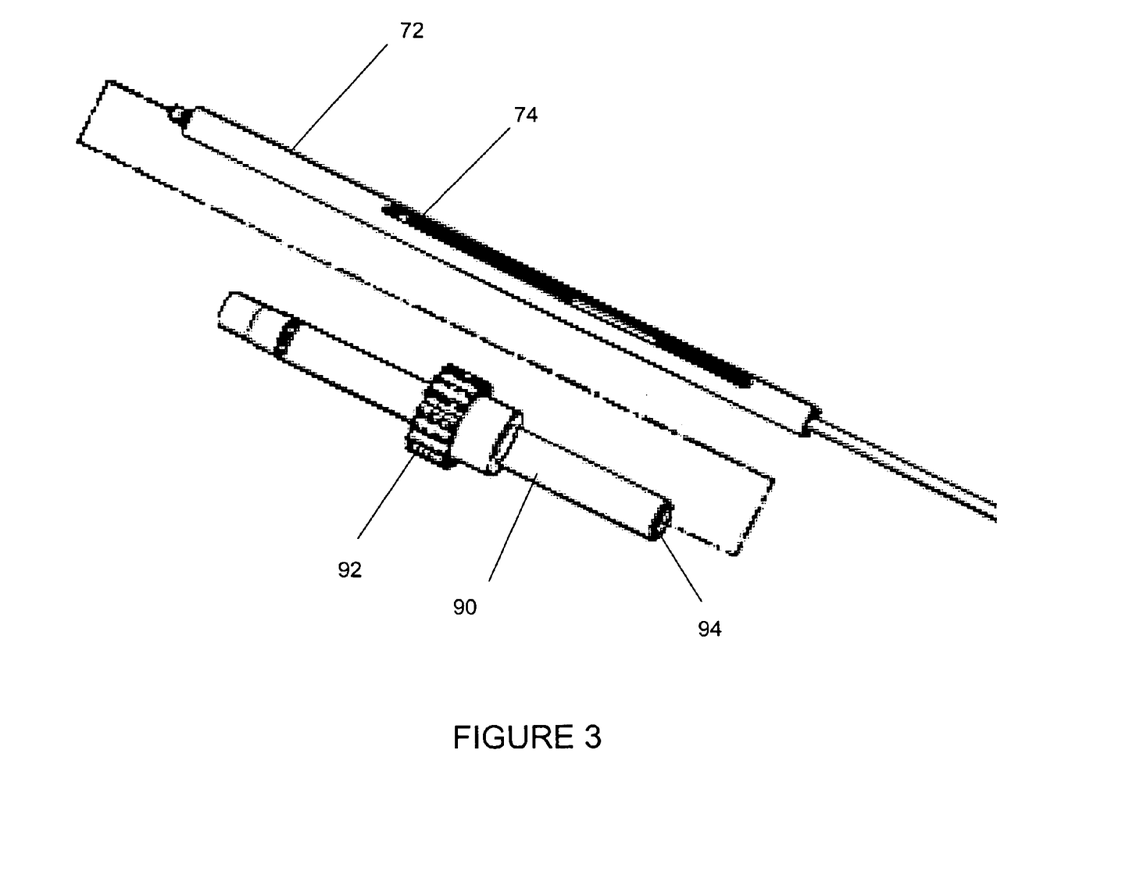
FIG. 3 is a schematic diagram of the pinion shaft exploded from the tubes.

The pinion encases at least the portion of the outer tube having the slot. As shown in FIG. 3, the pinion shaft 90 includes at least one gear 92 to operatively couple to the drive system gear. The pinion shaft includes a lumen 94 extending through the length of the pinion shaft. The diameter of the lumen is at least as large as the outer diameter of the outer tube 72, thereby allowing the tubes to extend through the lumen. The pinion shaft is at least as long as the length of the slot 74 of the outer tube along which the ball bearing may travel.

Figure 4A:
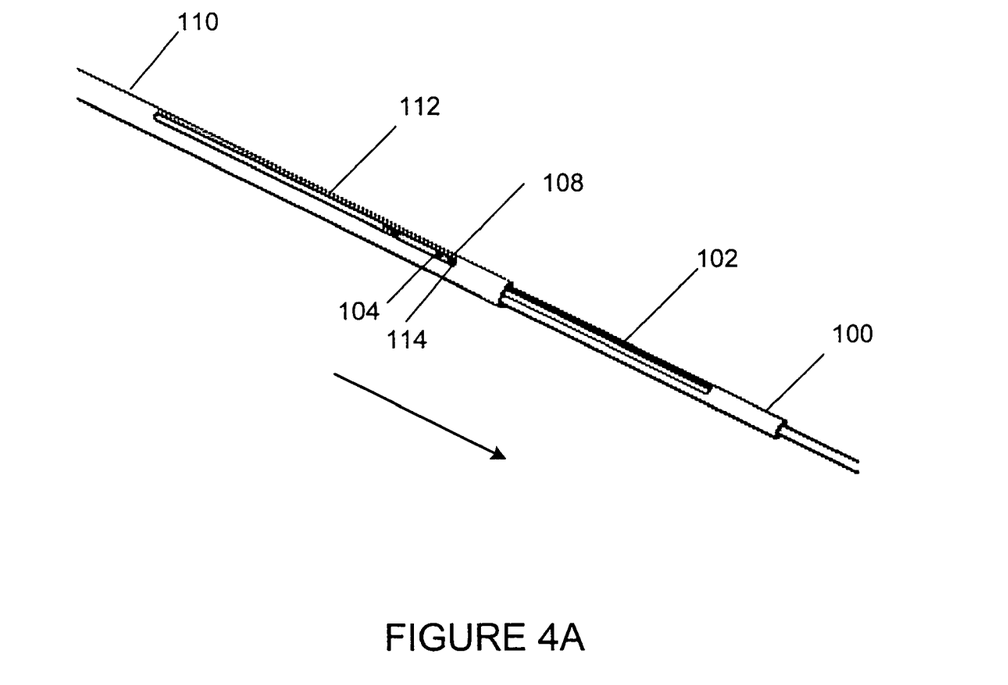

The longitudinal axis of the tubes is generally co-linear and the slot and tube align. The ball bearing maintains this slot/groove alignment by the ball's position between the side walls of both the slot and groove. As shown variously in FIGS. 4A and 4B, the inner tube slides laterally in relation to the outer tube. The slot and groove continue to line up as the system extends and retracts. The ball rolls within the slot and groove to permit the lateral movement of the inner tube relative to the outer tube. FIG. 4A shows an expanded transmission system in which an In order to axially translate the catheter system in a distal direction, i.e. deeper within the body, the inner tube slides in a distal direction away from the outer tube. As shown by the partial tubes in FIG. 4A, inner tube 100 is laterally slid in a distal direction, illustrated by the arrow, from the outer tube 110. In a fully expanded position, the ball 108 catches the distal end 114 of the slot 112 and the proximal end 102 of the groove 104. The contact between the ball and these two ends prevents further extension of the tubes.

In one embodiment, the length of the slot 112 dictates the distance in which the inner tube may slide in a distal direction. Any length of slot may be employed, depending, intra alia, on the extension of drive shaft required. For example, where the target site is farther away from the insertion site, i.e. deeper in the body, the slot may be longer. However, where a short slot is provided and more extension is required, a longer inner tube and groove may be employed to add extension length. In one embodiment, the length of the slot is between about 1.0-2.0 inches and more typically between about 1.0-1.50 inches, e.g. 1.21 inches. Where the slot and grove are equal lengths, the amounts of axial translation provided by the present system is often double the length of the slot or groove.

Figure 4B:
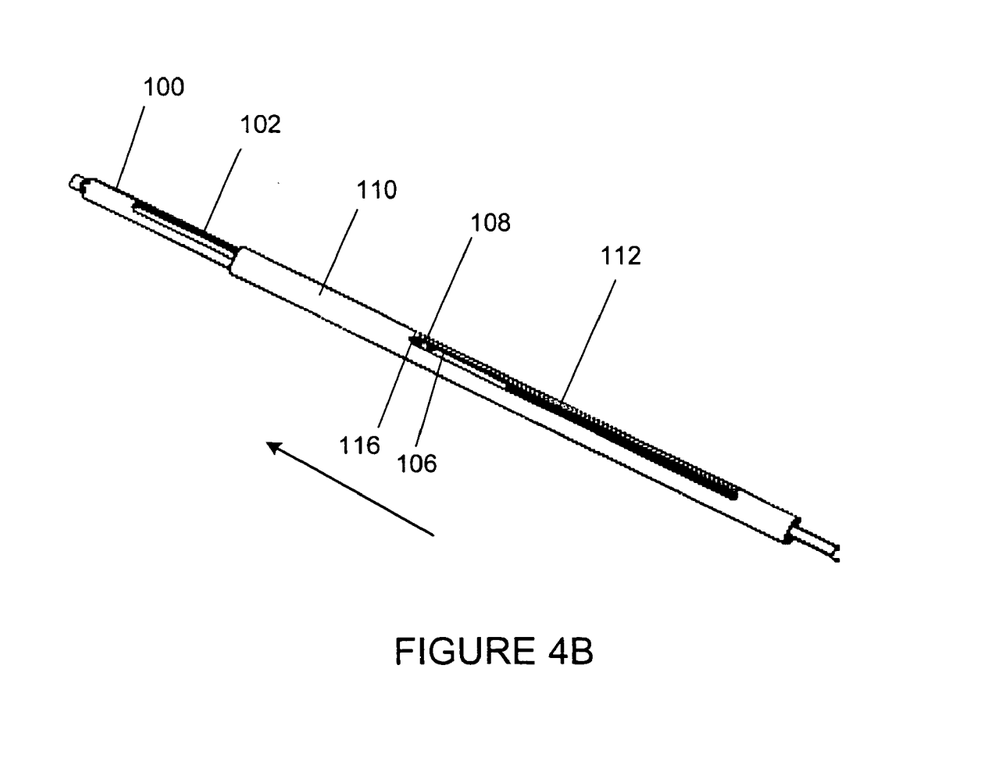

The system may be retracted, as illustrated by the fully retracted position of the tubes in FIG. 4. In this case the inner tube 100 sliding laterally in a proximal direct, as shown by the arrow, until the ball 108 catches the distal wall 106 of the inner tube groove 102 and the ball 108 catches the proximal end 116 of the slot 112 of outer tube 110.

In one embodiment, the length of the inner tube groove 102 determines, in part, the distance in which the inner tube may slide in a proximal direction. Any length of groove may be employed, depending, intra alia, on the length of the outer tube slot and the amount of retraction that is desired. In one embodiment, the length of the groove is between about 1.0-2.0 inches and more typically between about 1.0-1.50 inches, e.g. 1.10 inches.

Both the inner and outer tubes receive rotational torque. The pinion shaft conveys the torque from the drive shaft to the outer tube, and the ball engages the aligned canals of each tube to transfer rotational torque to the inner tube and the torque is conveyed to the drive shaft from the inner tube.

Figure 5A:
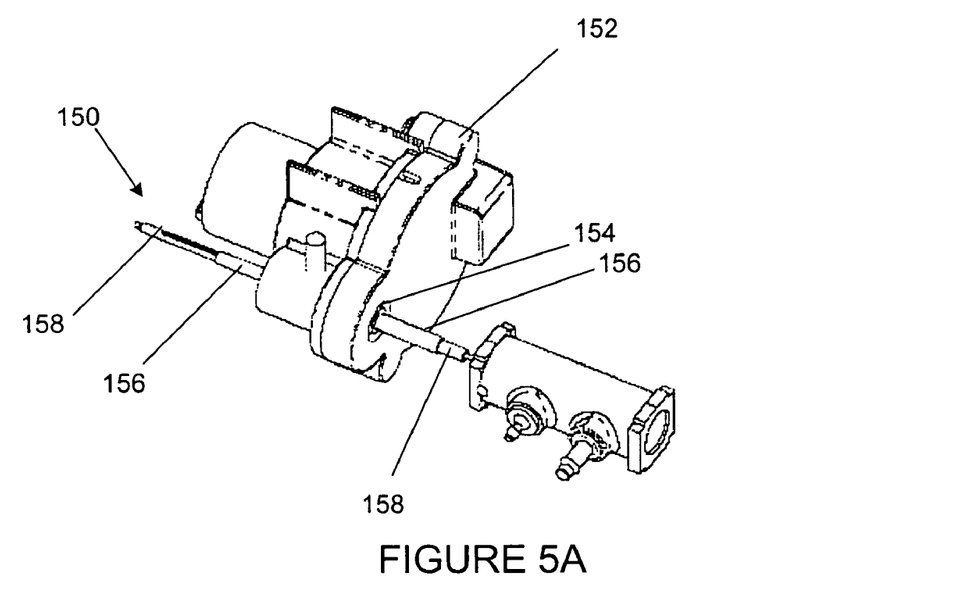
Figure 5B:
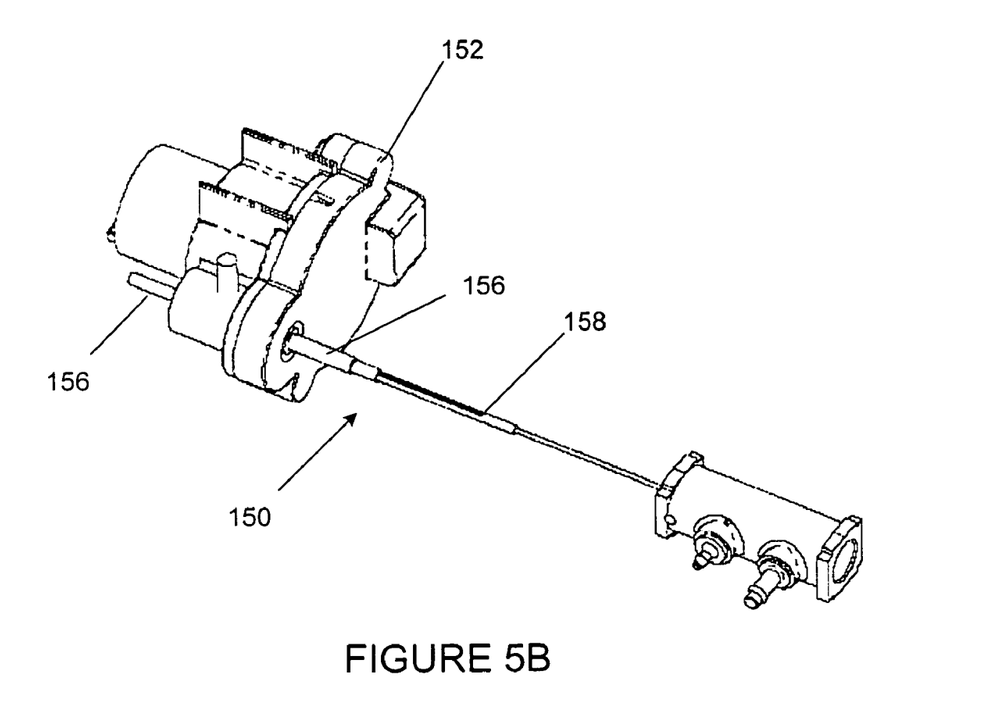

The transmission system is capable of conveying rotational torque while laterally moving. FIGS. 5A and 5B show lateral translation of the tubes while the system 150 is connected to the motor 152. The tubes extend through a lumen 154 of the housing of the motor. The outer tube 156 is held in a fixed position with regard to the motor. In moved to a retracted position as shown in FIG. 5A, the inner tube 158 is slidable through the outer tube and may extend out the distal end of the motor lumen 154. When in an extended position as shown in FIG. 5B, the inner tube 158 is slidable through the outer tube 156 and may not extend passed the distal end of the motor lumen 154. During extension or retraction of the system, the pinion shaft does not laterally translate with the inner tube movement.

Figure 6A:
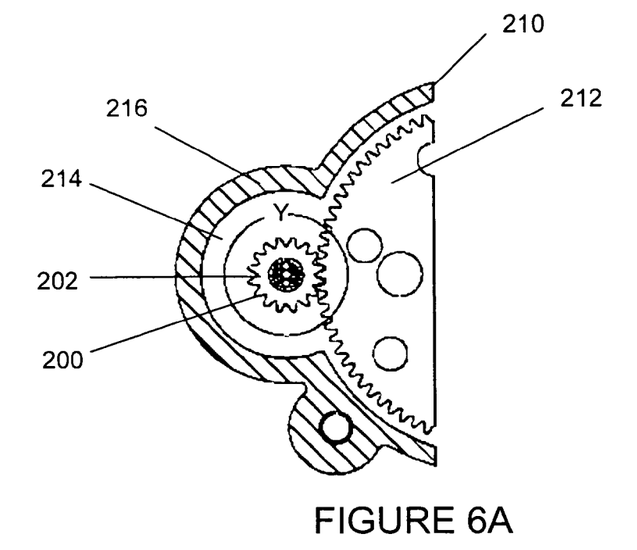
FIGS. 6A-6B are schematic diagrams of cross sectional internal views of a pinion shaft of the transmission system coupled to a drive system.
Figure 6B:
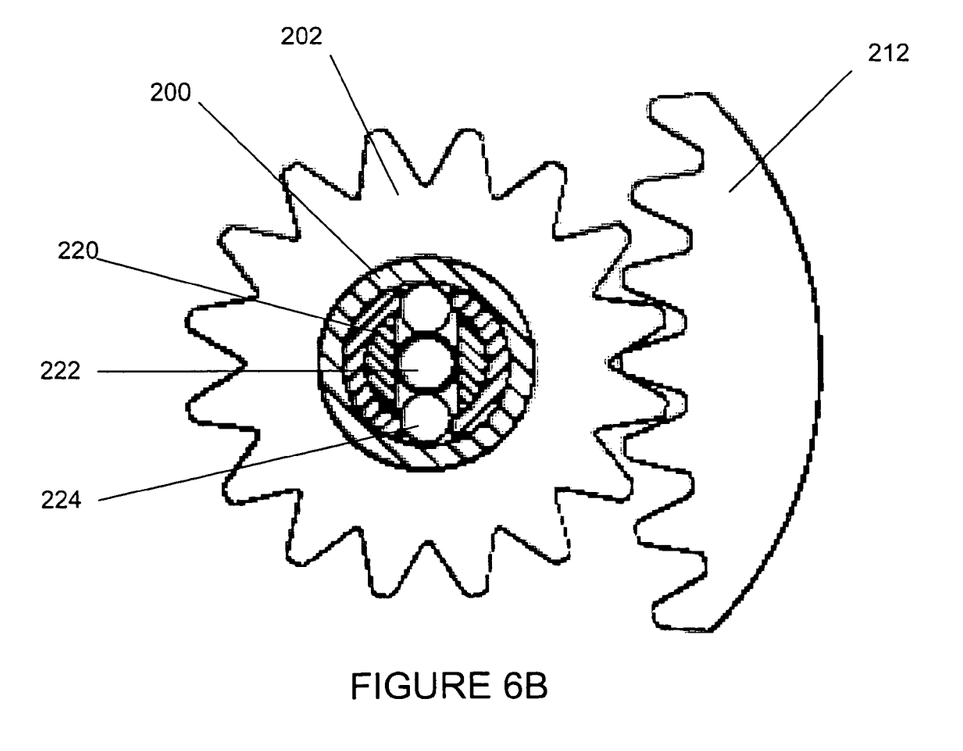

FIGS. 6A and 6B illustrate the engaging of the gear 202 of the pinion shaft 200 operatively engaged with the gear 212 of the drive system 210. The pinion shaft extends within the lumen 214 of the housing 216 of the drive system 210. An enlarged view of the gears (Y) of FIG. 6A is shown in FIG. 6B. Within the lumen 204 of the pinion shaft 200 resides the outer tube 220 and within the outer tube 220, resides the inner tube 222. The ball bearings 224 rest below the pinion shaft 200 and above the inner tube 222. The ball bearings are also placed within the outer tube 220.

Figure 7A:
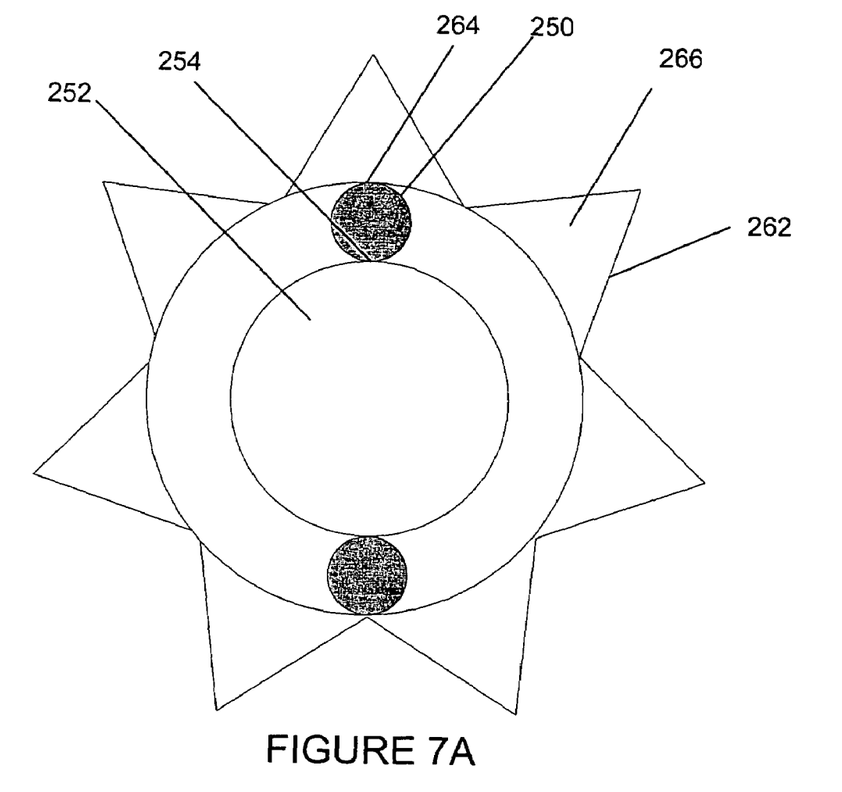
Figure 7B:
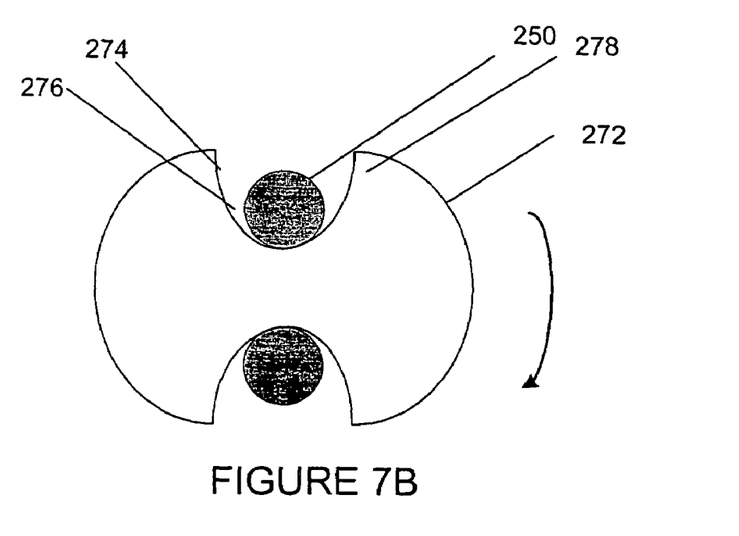

The position of the ball bearings relative to the tubes and pinion shaft is shown in FIGS. 7A and 7B. In particular, FIG. 7A illustrates the inner tube 252 having a surface 254 of its groove to provide an inner race in which the ball 250 may be seated to permit radial support of the ball. The groove is sized in width and pitch to allow the ball to rest in the bottom of the inner tube groove when the system is not operating. Outward radial motion of the ball 250 is further supported by the interior surface 264 of the pinion shaft 262. The pinion shaft has gear 266 on its exterior surface.

During operation of the medical device, the centrifugal force on the ball bearing as the system rotates usually urges the ball in an outward direction and the ball no longer rests within the bottom of the groove. The ball is then impelled against the pinion shaft surface. Furthermore, the torque forces the ball bearing to ride against an edge of the inner tube and an edge of the outer tube that are opposite of the direction of rotation.

FIG. 7B illustrates lateral support of the ball bearing 250 resting in the slot 274 of the outer tube 272. During rotation of the transmission system in the direction shown by the arrow, the ball rides against the slot side 276 and where rotation is in the opposite direction, the ball rides against the opposing slot side 278.

Figure 8:
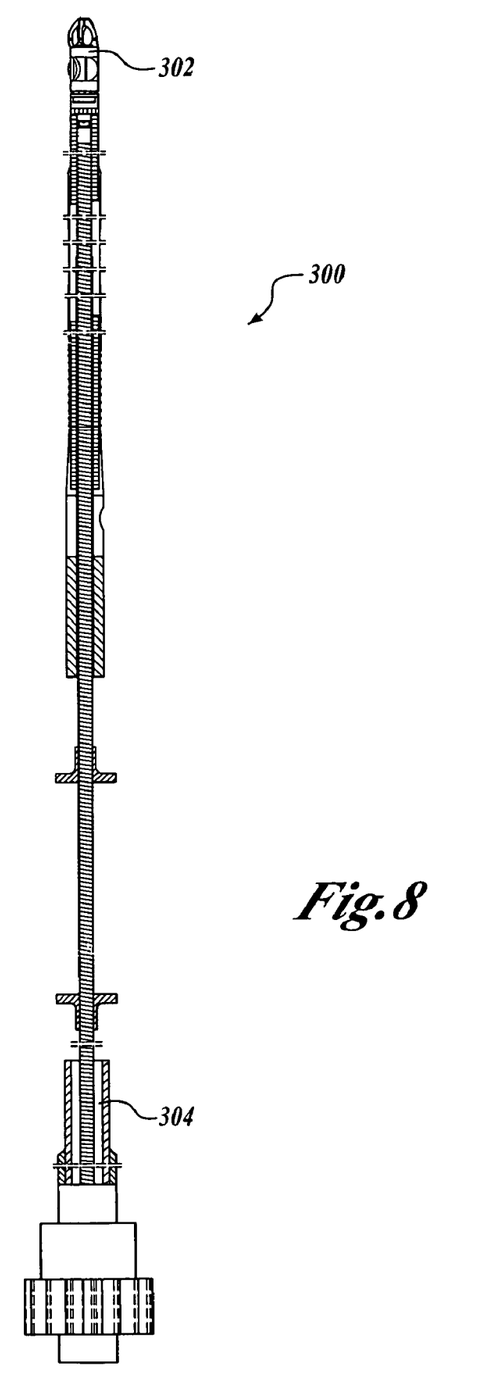
FIG. 8 is a schematic diagram of an intracorporeal device having an operating head.

One intracorporeal device that may incorporate the present torque transmission system 304 is shown in FIG. 8. The device 300 has an operating head 302 attached to a catheter that encloses a drive shaft. A wide variety of operating heads 302 for diagnostic or therapeutic surgical procedures within a body cavity that translates rotational torque from a drive shaft is well known to those skilled in the art. For example, types of intracorporeal devices may include an operating head that is a cutting head having one or more cutting surfaces, such as a rotary cutter with one or more blades or abrasives; a heating element for performing thermal ablation; electrodes for performing electrosurgical cutting and cauterization; abrasive elements for performing mechanical ablation; fluid jet stream tip; optical waveguides for performing laser ablation; ultrasonic transducers for imaging and ablation; angioscopic imaging devices; and the like.

One example of an intracorporeal device useful in diagnosis may include a probing operating head, such as an ultrasonic transducer. The diagnostic device may be useful in several medical fields. For example, in cardiology the operating head may be used to inspect the inside of the heart to identify abnormal structures or functions. The device may also be useful in measuring blood flow through the heart and other vessels. In urology, the device may be used to see kidney stones, measure blood flow through the kidney, detecting prostate cancer, etc.

In some particular applications of such an intracorporeal device, undesirable matter must be removed by maneuvering the intracorporeal device within the body cavity. If not removed, the matter may inhibit or cut off the flow of fluid, such as blood, and other essential components through the body cavity. For example, atherosclerosis is a condition arising from the deposition of fat-like matter, i.e. plaque, on the walls of blood vessels. As a result of accumulated obstructions, blood flow becomes restricted or blocked, creating health risks, including coronary artery disease, angina and heart attacks. The operating head for matter removal typically has one or more cutting surfaces, such as blades and/or abrasive coated burrs, which contact and ablate the matter. The drive shaft usually conveys high speed rotation, e.g. about 500 to 200,000 rpm's, such as about 40,000 rpm's, to the operating head to cause the cutting surfaces to ablate the matter. The intracorporeal matter removed by the present invention may be any unwanted material contained within a body cavity, such as artherosclerotic disease, calcified plaque, thrombus, a gallstone, and other debris, a body part such as a valve or portion thereof.

Figure 9:
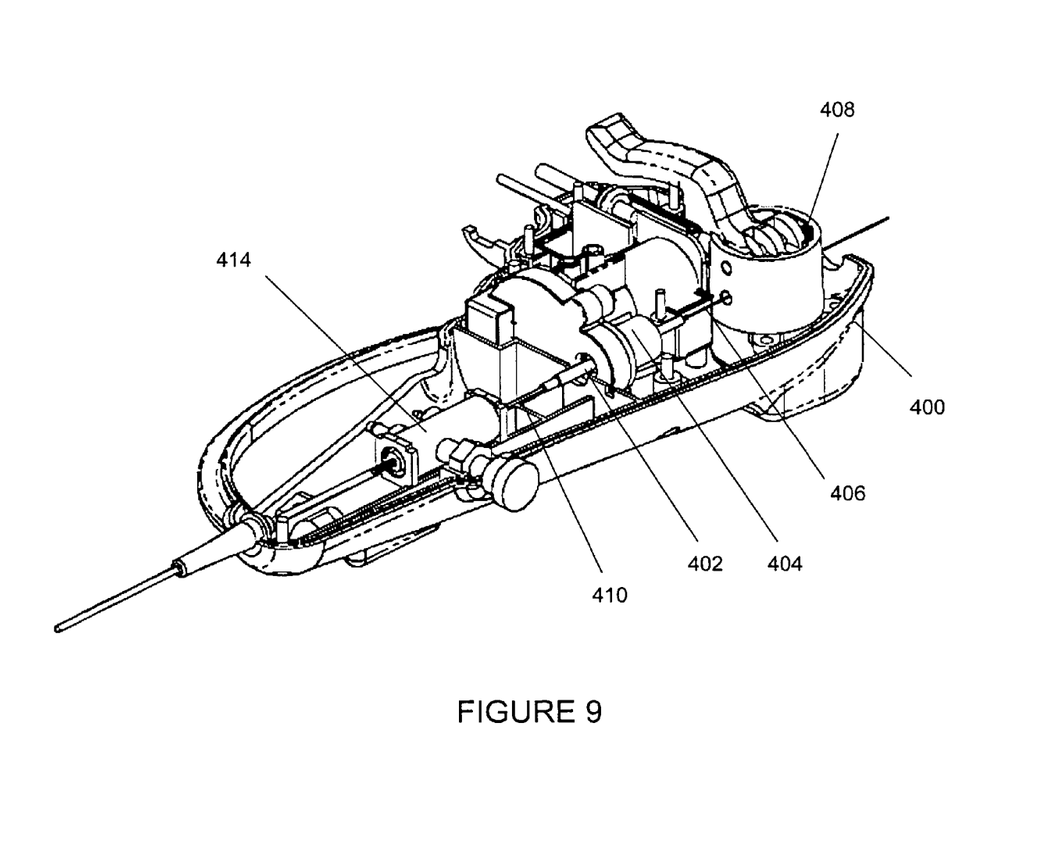
FIG. 9 is a schematic diagram illustrating a tracking pod housing a drive system.

Oftentimes, at least the transmission system and drive system are contained within a housing of the intracorporeal device, such as a hand held device. FIG. 9 shows one such hand held device, a tracking pod 400, housing the torque transmitting system 402 and drive system 404, as well as other components of the intracorporeal device. The transmission system extends through the drive system. A guide wire 406 may extend from the proximal end of the torque transmission system that exits the drive system and may engage with a guide wire lock 408. The guide wire 406 may continue through the guide wire lock 408 and out the back end of the tracking pod 400. The tracking pod may also include one or more drainage apertures and/or reservoirs to facilitate drainage of infusate, e.g. saline, from the sealing assembly.

Distal to the torque transmission system 402 is a drive shaft 410 extending into a sealing assembly 414. In one embodiment, the sealing member serves as a fluid-tight connector of catheter components including the drive shaft. The sealing member may also serve as a sliding extension member in which the sealing member may be slid within tracking pod, such as along a bed in the pod, in a distal and proximal direction in order to advance the catheter. In this case, the inner tube of the transmission system laterally moves to coincide with the lateral movement of the sealing member. Thus, when the sealing member is slid, so is the inner tube.

Where additional extension of the catheter and drive shaft are required, the sealing member is in a distal starting position and may be unlocked by sealing member lock 416. The guide wire clamp is also unlocked and the pod may be moved in a distal position along the guide wire. The sealing member and inner tube slide in a proximal direction as the pod is advanced until the sealing member reaches a proximal stop or the transmission system is retracted to its limit, whenever is occurs first. To advance the catheter/drive shaft further, the sealing member is repositioned to its starting position by unlocking the sealing member and sliding it in a distal direction until it reaches a stop or the transmission system is extended to its limit, whichever occurs first. The extending process may be repeated any number of times until there is no more available catheter length.

The tracking pod may be a convenient ergonomic design and constructed for placement in proximity to and/or in contact with the external body. In one embodiment, the tracking pod includes a handle for convenience in holding the tracking pod. The base of handheld unit may be configured, for example, to rest stably on the leg of a patient while a material removal operation takes place. The tracking pod according to the present invention is usually compact in size. The shape and size of the tracking pod often permits an operator to easily manipulate the drive shaft and/or catheter while holding the tracking pod. In one embodiment, the tracking pod is about 20 cm in length.

Figure 10:
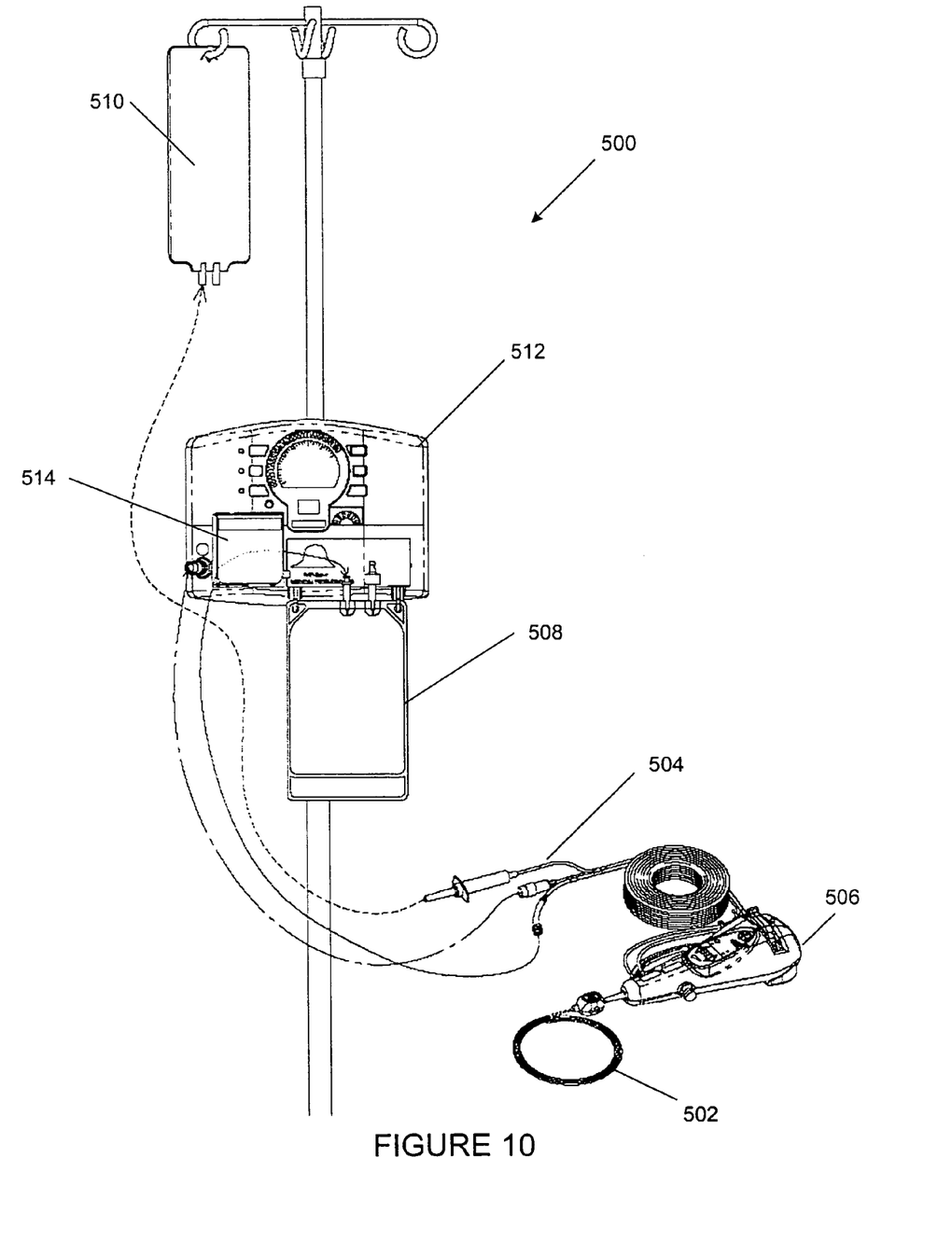
FIG. 10 is a schematic diagram of one type of an intracorporeal device that incorporating the torque transmission system.

FIG. 10 depicts an intracorporeal device 500 that may implement the torque transmission system within a hand held device 506, e.g. tracking pod. A catheter system 502 couples to an operating head at a distal end and a power source, e.g. drive system, at a proximal end, is provided. A tubing system 504 extends from the tracking pod, to a receiving container 508 that collects fluid and/or particles flowing from the catheter system. In addition, an infusate source 510 may also be provided to release fluid into the catheter system, when desired.

At the proximal location of the medical device, a console unit 512 may further be provided to receive control information from an operator and/or present operation information to the operator and direct control of the operating head, such as via control of the drive system power and/or voltage. The console unit 512 may also provide a power source for the motor and an aspiration source. The console unit may also be coupled to a variety of input devices for the operator to enter commands, such as a keyboard, personal data assistant, telephone, wireless communications devices, mouse, etc. Other communication features that are known or will be known in the future, for the operator to communicate with the console unit, either locally on the console unit or remotely, may be employed.

One or more pump(s) 514 may also be provided to provide aspiration for drawing materials from the catheter system and to receiving container 508. In one embodiment, console unit 512 and pump 514 are provided as a re-usable unit. In another embodiment, the hand held tracking pod 506 and control buttons may also be provided as a reusable unit. A more detailed description of one type of intracorporeal device in which the torque transmission system of the present invention may be used is provided in U.S. Pat. No. 6,565,588 B1, filed on Nov. 28, 2000 and in U.S. Provisional Patent Application No. 60/453,846.

The present invention has been described above in varied detail by reference to particular embodiments and figures. However, these specifics should not be construed as limitations on the scope of the invention, but merely as illustrations of some of the present embodiments. It is to be further understood that other modifications or substitutions may be made to the described the torque transmission system and medical device, as well as methods of their use without departing from the broad scope of the invention.

I claim:

1. A torque transmission system comprising:
    an outer tube having at least one longitudinal extending slot;
    an inner tube having at least one longitudinal extending groove aligned with the slot of the outer tube, the inner tube slidably engaged within the outer tube;
    a pinion shaft operatively coupled to a drive system and coupled to the outer tube to transfer rotational torque to the outer tube; and
    one or more ball bearing, each ball bearing rollably positioned within the slot and groove,
    wherein the ball bearing urges the inner tube to rotate as the outer tube rotates.

2. The system of claim 1, wherein the groove of the inner tube and the slot of the outer tube each include aligned side walls and the ball bearing biases against the aligned side walls to urge the inner tube to rotate.

3. The system of claim 1, wherein the groove of the inner tube includes a proximal end and the slot includes a distal end, and wherein the system is capable of extending by the inner tube sliding distally from the inner tube until the ball bearing catches the distal end of the slot and the proximal end of the groove.

4. The system of claim 1, further including a main shaft coupled to the inner tube and to a drive shaft.

5. The system of claim 1, wherein the width of the slot is slightly larger than the diameter of the ball bearing.

6. The system of claim 1, wherein the pinion shaft includes at least one gear operatively couple to the drive system gear.

7. An intracorporeal device comprising:
   a drive shaft;
   a drive system; and
   a torque transmission system comprising:
      an outer tube having at least one longitudinal extending slot;
      an inner tube with at least one longitudinal extending groove aligned with the slot of the outer tube, the inner tube slidably engaged within the outer tube;
      a pinion shaft operatively coupled to the drive system and coupled to the outer tube to transfer rotational torque to the outer tube; and
      one or more ball bearing, each ball bearing rollably positioned within the slot and groove,
   wherein the ball bearing urges the inner tube to rotate as the outer tube rotates and inner tube conveys the rotational torque to the drive shaft.

8. The system of claim 7, wherein the groove of the inner tube and the slot of the outer tube each include aligned side walls and the ball bearing biases against the aligned side walls to urge the inner tube to rotate.

9. The system of claim 8, wherein the groove of the inner tube includes a proximal end and the slot includes a distal end, and wherein the system is capable of extending by the inner tube sliding distally from the inner tube until the ball bearing catches the distal end of the slot and the proximal end of the groove.

10. The device of claim 7, further including a sealing member to slide in a movement that coincides with the sliding of the inner tube.

11. The device of claim 10, further including a hand held device to house the sealing member, drive system and transmission system.

12. The device of claim 8, further including a console unit to control the drive system.

* * * * *